United States Patent [19]

Poler

[11] 4,118,808

[45] Oct. 10, 1978

[54] INTRA-OCULAR LENS

[76] Inventor: Stanley Poler, 78 E. Second St., New York, N.Y. 10003

[21] Appl. No.: 862,027

[22] Filed: Dec. 19, 1977

Related U.S. Application Data

[62] Division of Ser. No. 691,033, May 28, 1976, Pat. No. 4,073,014.

[51] Int. Cl.$^2$ .......................... A61F 1/16; A61F 1/24
[52] U.S. Cl. ......................................................... 3/13
[58] Field of Search ......................................... 3/1, 13

[56] References Cited

U.S. PATENT DOCUMENTS

| | | | |
|---|---|---|---|
| 2,754,520 | 7/1956 | Crawford | 3/13 |
| 2,834,023 | 5/1958 | Lieb | 3/1 |
| 3,925,825 | 12/1975 | Richards et al. | 3/13 |
| 3,975,779 | 8/1976 | Richards et al. | 3/13 |

OTHER PUBLICATIONS

"Artiphakia and Aniseikonia," by Richard C. Troutman, American Journal of Ophthalmology, vol. 56, No. 2, Oct. 3-13, 1963, pp. 602-639.

*Primary Examiner*—Ronald L. Frinks
*Attorney, Agent, or Firm*—Hopgood, Calimafde, Kalil, Blaustein & Lieberman

[57] ABSTRACT

An improved lens implant for use in ophthalmological surgery, the lens being a replacement for a cataract-clouded natural lens, and the replacement being installed in the pupil at the iris as the operative step following removal of the cataracted lens. The invention features unitary adapter structure assembled to an intraocular lens element and having integrally formed first and second pluralities of radially outward stabilizing feet, in angularly spaced and interlaced relation, with the feet of the other plurality; and the respective pluralities of stabilizing feet are installed on opposite sides of the iris, thus enabling the iris to retain and position the implanted lens.

7 Claims, 14 Drawing Figures

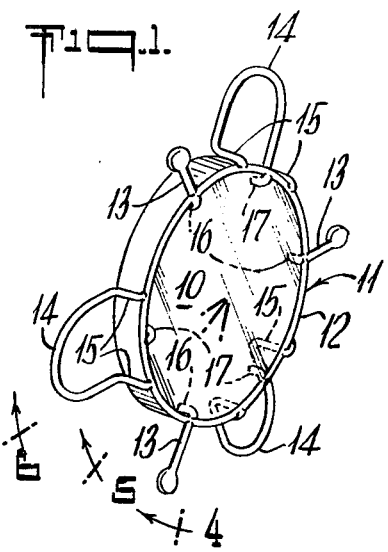
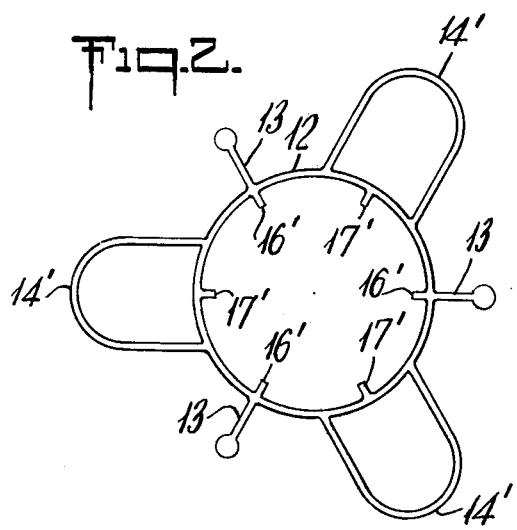
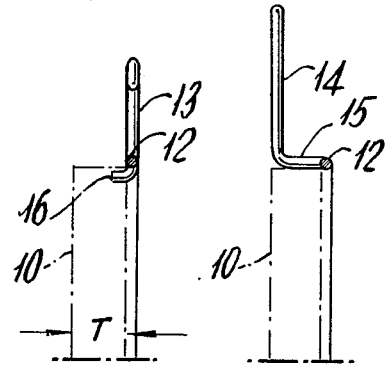
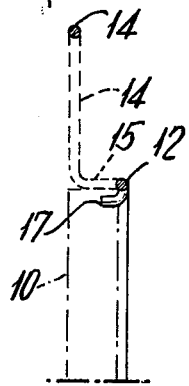
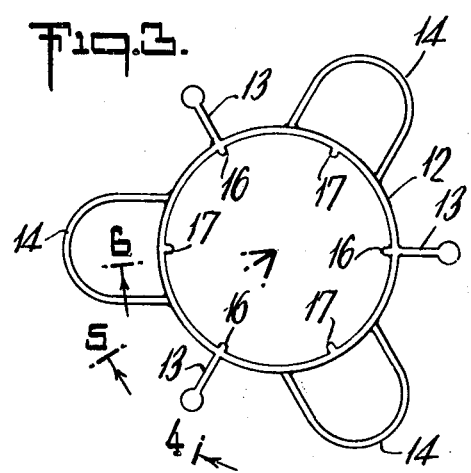
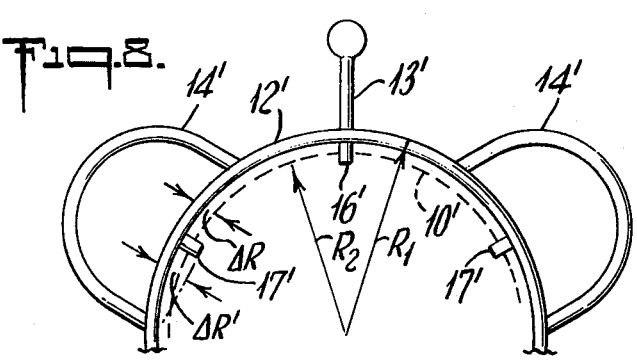
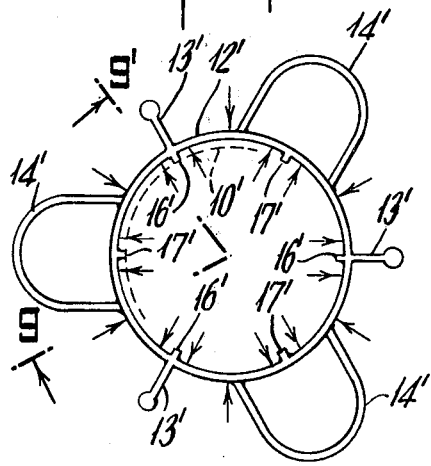
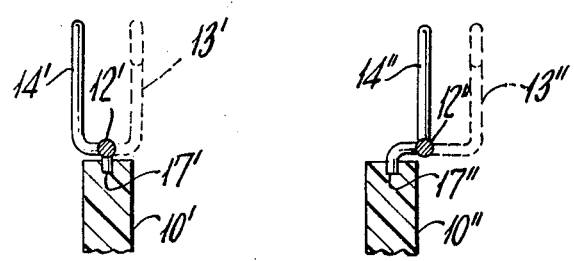
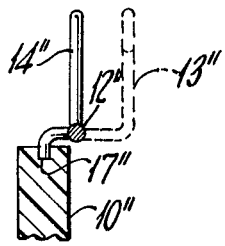

INTRA-OCULAR LENS

This application is a division of application Ser. No. 691,033 filed May 28, 1976, now U.S. Pat. No. 4,073,014.

The invention relates to an improved lens implant, as a replacement for a cataract-clouded or otherwise diseased natural lens.

As many as 500,000 Americans a year require surgery for removal of a natural lens which has become opaque (cataract), causing loss of vision. The modern therapy for cataract is surgical removal; this is generally done either by gently lifting the opaque lens from the eye in one piece, or by fragmenting the lens and washing out the fragments. When the cataractous lens is removed, an alternate method must be provided to focus light entering the eye, so that a sharp image focuses at the retina. Strong spectacle lenses and contact lenses are both commonly used for this purpose, but both have important shortcomings. Strong spectacle lenses tremendously enlarge the image, foreshorten distances, restrict peripheral vision, and prevent both eyes from being used simultaneously if both eyes have not had cataract surgery; contact lenses overcome some of these problems but introduce others, involved in insertion, removal and frequent maintenance.

The concept of implanting an intra-ocular lens in place of the removed natural lens is not new, although it is of relatively recent origin. To date, however, a significant limitation on such a procedure has been the relative unavailability of implant lenses, for their production has relied upon small, craft-style workshops, and lens quality has been less than satisfactory.

It is accordingly an object of the invention to provide an improved intra-ocular lens, for implant procedures of the character indicated.

Another object is to provide improved mounting structure for such lenses, whereby operative procedures may be more safely and reliably performed.

It is also an object to provide such lenses complete with mounting structure, of inherent high quality, adherence to specifications, and reproducibility by precision mass-production techniques.

Other objects and various further features of novelty and invention will be pointed out or will occur to those skilled in the art from a reading of the following specification, in conjunction with the accompanying drawings. In said drawings, which show, for illustrative purposes only, preferred forms of the invention:

FIG. 1 is an enlarged view in perspective, showing an intra-ocular lens and unitary mount of the invention, ready for operative implantation, as in the course of a cataract operation;

FIGS. 2 and 3 are plan views of the unitary mount of FIG. 1, FIG. 2 being to show an interim formative condition, and FIG. 3 showing the fully formed mount ready for assembly to the lens element;

Figure 11:
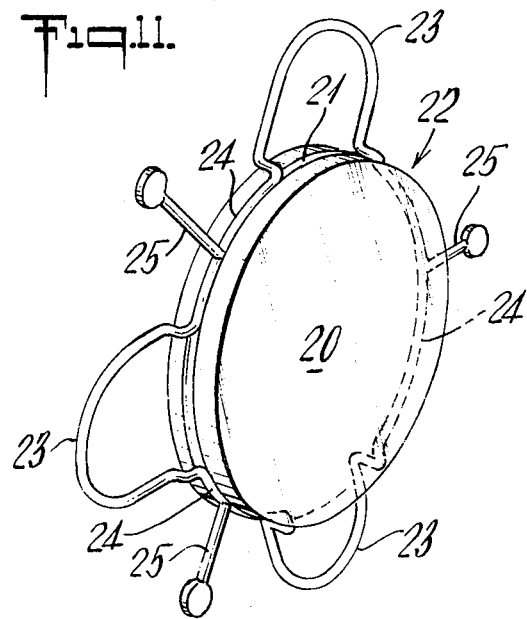
Figure 12:
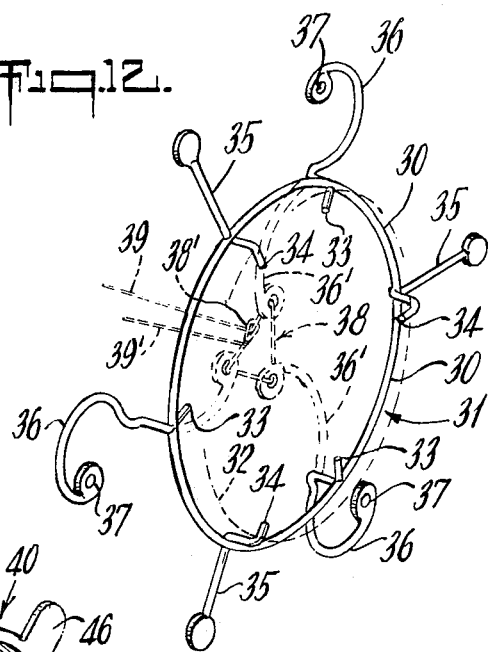

FIGS. 4, 5 and 6 are fragmentary sectional views taken at the planes 4, 5 and 6 indicated in FIGS. 1 and 3;

FIG. 7 is a view similar to FIG. 3 to show a modification;

FIG. 8 is an enlarged fragmentary view of the structure of FIG. 7, to permit identification of dimensional features;

FIG. 9 is a fragmentary sectional view, with solid outlines as taken at the plane 9, and with phantom outlines as taken at the plane 9' of FIG. 7;

FIG. 10 is a view similar to FIG. 9 to show a modification;

FIGS. 11 and 12 are perspective views to show further modifications; and

Figure 13:
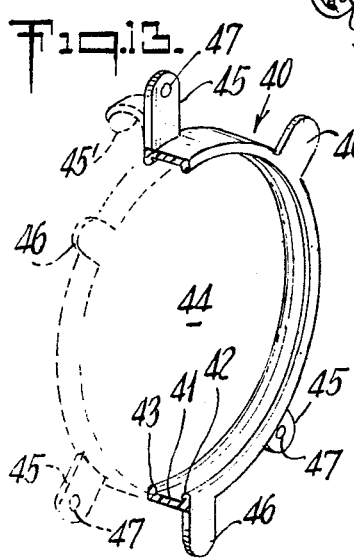
Figure 14:
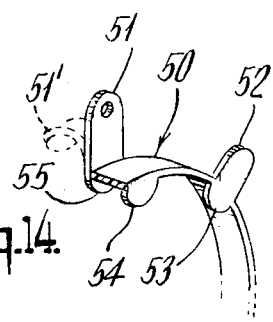

FIGS. 13 and 14 are fragmentary views in perspective to show still further modifications.

Referring to FIGS. 1 to 6, the invention is shown in application to an implant lens 10 of non-toxic transparent plastic, such as methylmethacrylate. Lens 10 is of such refractive index and is so ground that when mounted at the iris and immersed in the intra-ocular, the thus-implanted eye will develop sharp image focus at the retina. Lens 10 is typically although not necessarily circular about its optical axis; it may, for example, be of 5-mm diameter and have a peripheral-edge thickness T of 1-mm or less.

In accordance with the invention, unitary mounting structure 11 is secured to lens 10 and provides first and second pluralities of radially outward feet for axially stabilized positioning reference to the iris, the feet of one plurality being axially offset from and angularly interlaced with those of the other plurality, so that both sides of the iris contribute to stability. As shown, a circumferentially continuous ring 12 conforms to the peripheral contour of the edge of lens 10, being positioned adjacent one face of the lens. The first plurality of feet comprises three angularly spaced rods 13 extending radially outward for retention adjacent the outer side (anterior surface) of the iris, with the pupilary border of the iris itself closing upon the circular edge of the lens. The second plurality of feet comprises three radially outward loops 14 in a radial plane which is axially offset from ring 12, to substantially the extent T. Thus, each of the feet 14 includes two spaced short offset leg portions 15 which engage the circular edge of lens 10, and the radial loop portion extends from the leg portions 15. For the case of the plastic lens 10 of FIG. 1, six L-shaped anchoring prongs 16–17 extend first radially inwardly and then axially rearwardly, the same being embedded into adjacent rim regions of the lens 10.

The described mounting structure or adapter 11 is preferably a single piece of metal, with all anchoring prongs 16–17 and stabilizing feet 13–14 integrally formed with the body ring 12. The metal is inert to body tissue and fluids and is suitably stainless steel, of thickness in the order of 0.1-mm. I have found it practical to construct the "blank" of FIG. 2, for the mounting structure 11, by employing photographic and etching techniques.

More specifically, for the case of the "blank" of FIG. 2, a drawing was initially prepared, to greatly enlarged scale, e.g., 40 times. This drawing was photographically reduced to ultimate size, and multiplied at indexed locations to produce a photographic negative with plural reduced images of the drawing. Then, one of a class of metals which was tolerated by the body (e.g., stainless steel, platinum, irridium, etc.) was coated with a photosensitive material. The negative was placed in contact with the photosensititive coat, exposed to light, and then developed in a "photographic reversal", thus removing from the exposed surface those areas which have been exposed to light. The sheet that was left was then placed in a chemical solution (ferric chloride) which etched away unwanted material, leaving only a completed profile of the "blank". The described etching process has the advantage that it tends to produce round, burr-free edges, and it can use materials that are lighter and thinner than anything which to my knowledge and belief has been available to date.

FIG. 2 depicts the "blank" thus prepared, it being noted that lobes 14' are of extended radial projection, in order to account both for the offsets 15 and the lobes 14; by the same token, the barbs 16'-17' are of extended inward radial projection, in order to account for both the radially inward and the axially inward leg portions of prongs 16-17. Bending dies are employed to operate upon the "blank" of FIG. 2, such that all necessary axial offsets are produced, resulting in reduction of the overall circle defined by legs 14 and expansion of the circle defined by prongs 16-17, all as appears from comparison of the "before" and "after" plan views of FIGS. 2 and 3.

To complete the description of an actual physical embodiment of FIGS. 1 to 6, I indicate that each of the retaining rod-like feet 13 terminates with a small knob formation, to avoid presentation of any sharp edge to irritate iris tissue. These knobs are on a circle of 7.5-mm diameter, and the outer limits of legs 14 are on a circle of 8-mm diameter. The prongs 16-17 are bent axially at a location radially inwardly offset about 0.15-mm from the body ring 12; they are embedded into lens 10 to the extent of about 0.30-mm in the axial direction. Such embedding may be accomplished without drilling, by axially directed ultrasonic driving impulses applied at prongs 16-17, while retaining ring (12) and leg (13-14) parts of the adapter 11 in damped condition. The optical distortion of lens 10 due to such driven assembly of the adapter to the lens is negligible.

In the embodiment of FIGS. 7 to 9, the layout of the adapter "blank" is generally as described for FIG. 2, with the exception that the radius $R_1$ of the body ring 12' exceeds the radius $R_2$ of the lens 10' about its optical axis to an extent $\Delta R$ which is slightly less than the effective radially inwardly projecting extent $\Delta R'$ of the anchoring barbs 16'-17'. The interlaced pluralities of radially outward stabilizing feet 13'-14' are in axially offset relation, each plurality being offset in the direction opposite the other plurality, as is apparent from FIG. 9. To assemble the adapter of FIG. 7 to its lens 10', the body ring 12' is transiently distorted by suitable tooling, in approach to a polygonal shape; the action of such tooling is denoted by radially inward and radially outward arrows which symbolize local force application to transiently radially outwardly displace all barbs 16'-17' to clear the outer-edge on rim radius $R_2$ of lens 10'. Once axially centered around this rim, the tooling is relaxed to allow compliant restoration of ring 12' to its circular profile; in the course of such restoration, barbs 16'-17' contact the lens rim and are then driven into short radial local embedment in the lens, as by ultrasonic tool means. The assembly is then complete and ready for sterilization and implantation.

FIG. 10 illustrates a slight modification of FIGS. 7 to 9, wherein the ring body 12" is at one axial end of lens 10" and the pluralities of stabilizing feet 13"-14" determine iris retention in a plane that is axially offset from lens 10". The barbs 16"-17" are longer than previously described, to permit an axially offsetting projection from ring 12" before radially inward bending to engage and become locally radially embedded at spaced locations along the rim of lens 10".

In the embodiment of FIG. 11, the rim of lens 20 has a peripheral groove 21, and the unitary mounting adapter 22 is so formed as to permanently assemble by resilient snap action into the groove 21. Adapter 22 may still be formed from a single peice "blank" by the indicated photo-chemical technique, and it may still be a circumferentially continuous structure. As shown, the looped legs 23 comprising one plurality of locating feet integrally connect adjacent ends of spaced body-ring arcs 24, and the rod-like feet 25 of the other plurality extend radially from the respective arcs 24; axial offset of these pluralities is built into legs 23, in the manner generally as described at 15 in FIG. 1, except for a small initial radially outward offset in such legs 23 at juncture with arcs 24. In unstressed condition, the arcs 24 are of curvature conforming to that of groove 21 and are preferably at a slight radially inwardly displaced position with respect to the circle of groove 21. To assemble to lens 20, arcs 24 are outwardly spread against the compliant action of loops 23, in order to permit placement and resilient snap retention of arcs 24 in groove 21. The assembly is then ready for sterilization and implantation.

In the embodiment of FIG. 12, the circular body ring 30 of a unitary adapter 31 is retained in its assembly to a lens 32 by radially inward barbs 33-34 of one plurality (33) which engage over one axial end of lens 32 and of another plurality (34) interlaced with the barbs of the first plurality and engaging over the other axial end of lens 32, thus retaining the assembly without resort to mechanical embedment in lens material.

As shown, the iris-stabilizing feet 35 of one plurality are spaced radial rods at the ring locations of barbs 34, and barbs 34 include axial offsets to the extent of lens-rim thickness. The feet 36 of the other plurality include axial offsets at juncture to the body ring 30, at which locations barbs 33 also extend radially inward. Feet 36 differ from the loops already described in that they are somewhat coiled or looped in a common radial plane, the free end of the coil being apertured at 37. FIG. 12 will be understood to depict the unstressed normal condition and orientation of feet 36.

In accordance with a feature of the invention, the inherent resilient compliance of feet 36 and their apertured ends 37 are employed to facilitate operative insertion through the pupil of the iris. In preparation, a suture 38 such as a filament of nylon is tied with a loop 38' intermediate its free ends 39-39'. The end 39 is threaded through all foot apertures 37 before passing through loop 38' and is then tightened, to radially inwardly compliantly draw all foot ends 37 to within the peripheral confines of lens 30, as denoted by phantom outlines 36' in FIG. 12. In operative insertion of the retracted legs 36 past the pupil, the suture ends 39-39' are held back, the end 39 being tightly held until release when legs 36 are safely behind the iris. Upon release of the end 39, the other end 39' is drawn, thereby first withdrawing the loop 38' and allowing the remaining end 39 to pull out of loop 38' and all apertures 37 before complete removal of the suture.

FIGS. 13 and 14 are fragmentary perspective views to illustrate alternative lens adapter structures which may be of molded or etched or otherwise formed inert plastic, such as nylon. In FIG. 13, a peripherally continuous ring 40 is characterized by a bore in the nature of a continuous radially inwardly facing channel or groove 41 between side walls or ribs 42-43. The width and effective depth of groove 41 are such as to securely retain a lens 44 assembled thereto, it being understood that the ring plastic is sufficiently compliant to enable the local transient deformation necessary to accomplish lens assembly to groove 41. First and second axially offset pluralities of iris-engaging feet 45–46 extend from the axial end faces of ring 40 in interlaced relation. The feet 45 of one of these pluralities are shown apertured at 47 to facilitate correct end-for-end recognition by the surgeon. Apertures 47 will also be understood to serve the suture technique described in connection with FIG. 12, it being understood that feet 45 would be thereby deflected by radially inward bending as suggested by phantom outline 45' in FIG. 13. Upon release of the suture behind the iris, the memory of the plastic will restore feet 45 to the orientation shown in solid outline.

The embodiment of FIG. 14 differs from FIG. 13 in the absence of a groove formation in the plastic body ring 50. First and second pluralities of axially offset positioning feet 51–52 extend radially from the body 50. Lens retention is via plural spaced radially inward lugs 53–54 at one axial end and via plural similar lugs 55 at the other axial end. Lugs 53 are formed at locations of feet 52, and lugs 54 are at angular locations of feet 51, being axially offset therefrom. Preferably, each lug 55 is formed as an integral inward extension of the corresponding foot 51, so that in the sense of FIG. 14, a clockwise deflection of a foot 51 produces a transient retraction of the corresponding lug 55, thereby facilitating lens insertion and assembly, as will be understood. Feet 51 are shown apertured as described for feet 45 in FIG. 13, for suture deflection as suggested by the inwardly deflected position shown at phantom outline 51'.

It will be seen that I have described intra-ocular lens and mount structures meeting all stated objects and, importantly, lending themselves to mass-production techniques, of inherent precision and control. The drilling operations previously considered necessary have been totally avoided, as has also the reliance upon multiple parts, thus simplifying manufacturing and avoiding generation of waste particles. While plastic lenses have been specifically mentioned in several illustrative contents, it will be appreciated that the invention is not necessarily limited to such use. For example, glass lenses are to be preferred and certainly can be well and safely mounted, using structures of FIGS. 11 to 14. Also, although circular lens body-ring peripheral contours have been described for all forms, it will be appreciated that this was purely to simplify description, in that the described techniques and structures have equal application whatever the peripheral contour of the lens; for example, an oval lens-rim contour may be selected for more ready operative insertion past the pupil, for certain patient requirements, and to reduce the chance of surgical trauma. Still further, the inherent nature of the mounted lenses of the invention is such that an absolute minimum of structure ever protrudes into the anterior chamber of the eye; thus, danger of corneal-tissue contact with any part of the intra-ocular lens structure of the invention is substantially less than that with prior art structures. For the disclosed forms of the invention wherein the iris closes on a circular lens periphery, there is minimal stress on the sphincter muscle, with attendant reduced risk of trauma.

While the invention has been described in detail for the preferred forms shown, it will be understood that modifications may be made within the scope of the invention. For example, the reference to metal for the adapter structures of FIGS. 11 and 12 will be understood to be illustrative, since similarly formed and suitably stiff and non-toxic plastics may also serve the same purpose. Also, the reference to photochemical preparation of metal "blanks" is illustrative of a preferred technique, in that photo-resist and plating techniques of the printed-circuit technology, with subsequent release from a substrate, may also be employed.

Also, while metal ring structures have been disclosed in combination with the lens element thereby mounted, it will be understood that unitary metal structure may be, and in certain cases preferably is, subjected to an inert protective coating of a plastic material such as nylon, thus assuring against any possibility of a minute metal burr or barb projecting for body-tissue contact.

Still further, it will be understood that the glass used in the lens element mounted by my invention may be of phototropic material, thus providing a degree of automatic self-regularing accommodation to existing light conditions and, to a degree, supplementing and replacing light-regulating functions previously handled by iris action alone.

What is claimed is:

1. As an article of manufacture, an optically finished intra-ocular lens element having a continuous periphery about its optical axis, and a flexibly compliant single-piece plastic mounting adapter therefor, said adapter comprising a peripherally continuous ring body surrounding the periphery of said lens element, axially spaced lens-retaining formations integral with said ring body and extending directly inwardly from said body in retaining engagement with both axial sides of the periphery of said lens element, and first and second pluralities of lens-positioning feet integral with said ring body and radially outwardly extending therefrom in angularly spaced and interlaced relation, the feet of one plurality being in axially offset relation to the feet of the other plurality.

2. As an article of manufacture, a single-piece unitary plastic mounting adapter for iris-stabilized mounting of an intra-ocular lens element, comprising a circumferentially continuous ring body of peripheral contour generally conforming to and adapted to surround the peripheral contour of the lens element, plural axially spaced lens-retaining formations integral, with said ring body and extending directly inwardly from said body for axially limiting retaining engagement with both axial sides of the periphery of the lens element, and first and second pluralities of lens-positioning feet integral with said ring body and radially outwardly extending therefrom in angularly spaced and interlaced relation, the feet of one plurality being in axially offset relation to the feet of the other plurality, whereby at least one foot of said one plurality of feet may be resiliently stressed and inwardly deformed at reduced radial offset from the ring-body axis in the course of insertion via an iris opening, and further whereby such a deformed foot may thereafter be released for compliant restoration of its unstressed radially outward orientation behind the iris opening.

3. The article of claim 2, in which said inwardly extending retaining formations include a circumferentially continuous flange for engaging one axial side of the periphery of the lens element.

4. The article of claim 2, in which said inwardly extending retaining formations comprise two axially spaced substantially continuous circumferential flanges for engaging the respective axial sides of the periphery of the lens element.

5. The article of claim 2, in which said inwardly extending retaining formations include at one axial location a plurality of angularly spaced radially inward lug formations.

6. The article of claim 5, in which at least some of said feet are radially continuously formed with some of said retaining formations at substantially the same axially located plane and at substantially the same angular location in said plane.

7. The article of claim 2, in which at least one of said feet has an aperture near the radially outer limit of said one foot.

* * * * *